(12) United States Patent
Ho (10) Patent No.: US 9,700,410 B2
(45) Date of Patent: Jul. 11, 2017

(54) METHOD AND APPARATUS FOR PERCUTANEOUS AORTIC VALVE REPLACEMENT

(71) Applicant: HOCOR Cardiovascular Technologies LLC, Honolulu, HI (US)

(72) Inventor: Paul C. Ho, Honolulu, HI (US)

(73) Assignee: HOCOR Cardiovascular Technologies LLC, Honolulu, HI (US)

( * ) Notice: Subject to any disclaimer, the term of this patent is extended or adjusted under 35 U.S.C. 154(b) by 110 days.

(21) Appl. No.: 14/155,060

(22) Filed: Jan. 14, 2014

(65) Prior Publication Data

US 2014/0200658 A1    Jul. 17, 2014

Related U.S. Application Data

(63) Continuation of application No. 11/781,924, filed on Jul. 23, 2007, now Pat. No. 8,663,318.

(51) Int. Cl.
*A61F 2/24* (2006.01)
*A61B 17/12* (2006.01)
*A61B 17/22* (2006.01)

(52) U.S. Cl.
CPC ........ *A61F 2/2433* (2013.01); *A61B 17/1204* (2013.01); *A61B 17/12022* (2013.01); *A61B 17/12136* (2013.01); *A61F 2/2418* (2013.01); *A61B 2017/22055* (2013.01); *A61B 2017/22067* (2013.01); *A61F 2250/0059* (2013.01)

(58) Field of Classification Search
CPC ...... A61F 2/247; A61F 2/2433; A61F 2/2418; A61F 2/24; A61F 2250/0059; A61F 2250/0063; A61B 17/12022; A61B 17/12027; A61B 17/1204; A61B 17/12136; A61B 17/12122; A61B 2017/22055; A61B 2017/22067
See application file for complete search history.

(56) References Cited

U.S. PATENT DOCUMENTS

| 3,671,979 A | 6/1972 | Moulopoulos |
| 4,056,854 A | 11/1977 | Boretos et al. |
| 4,705,507 A | 11/1987 | Boyles |

(Continued)

FOREIGN PATENT DOCUMENTS

| WO | WO 00/44313 A1 | 8/2000 |
| WO | WO 00/47139 A1 | 8/2000 |

(Continued)

OTHER PUBLICATIONS

U.S. Appl. No. 14/154,890, filed Jan. 14, 2014, Ho.

(Continued)

*Primary Examiner* — Melanie Tyson
(74) *Attorney, Agent, or Firm* — Wilson Sonsini Goodrich & Rosati (57) ABSTRACT

A catheter adapted for placement in the ascending aorta comprises a central catheter mechanism and a balloon structure or other occluding structure at its distal end. The catheter may be placed over the aortic arch such that the occluding structure is placed in the ascending aorta just above the Sinus of Valsalva and coronary ostia. Once in place, the occluding structure is inflated to control blood flow through the aorta during aortic valve ablation and replacement protocols.

24 Claims, 4 Drawing Sheets

(56) References Cited

U.S. PATENT DOCUMENTS

| | | | |
|---|---|---|---|
| 4,787,388 | A | 11/1988 | Hofmann |
| 4,816,029 | A | 3/1989 | Penny |
| 4,878,495 | A | 11/1989 | Grayzel |
| 5,295,960 | A | 3/1994 | Aliahmad et al. |
| 5,308,323 | A | 5/1994 | Sogawa et al. |
| 5,308,356 | A | 5/1994 | Blackshear, Jr. et al. |
| 5,383,856 | A | 1/1995 | Bersin |
| 5,403,280 | A | 4/1995 | Wang |
| 5,411,552 | A | 5/1995 | Andersen et al. |
| 5,458,575 | A | 10/1995 | Wang |
| 5,505,702 | A | 4/1996 | Arney |
| 5,645,529 | A | 7/1997 | Fagan et al. |
| 5,718,684 | A | 2/1998 | Gupta |
| 5,792,300 | A | 8/1998 | Inderbitzen et al. |
| 5,827,321 | A | 10/1998 | Roubin et al. |
| 5,910,103 | A | 6/1999 | Saper |
| 5,938,582 | A | 8/1999 | Ciamacco, Jr. et al. |
| 6,068,611 | A | 5/2000 | Loffler et al. |
| 6,117,064 | A | 9/2000 | Apple et al. |
| 6,234,952 | B1 | 5/2001 | Liprie |
| 6,425,916 | B1 * | 7/2002 | Garrison et al. ............ 623/2.11 |
| 6,482,228 | B1 | 11/2002 | Norred |
| 6,540,734 | B1 | 4/2003 | Chiu et al. |
| 6,544,224 | B1 | 4/2003 | Steese-Bradley |
| 6,610,083 | B2 | 8/2003 | Keller et al. |
| 6,656,714 | B2 | 12/2003 | Hedge |
| 6,709,440 | B2 | 3/2004 | Callol et al. |
| 6,761,731 | B2 | 7/2004 | Majercak |
| 6,769,434 | B2 | 8/2004 | Liddicoat et al. |
| 6,835,188 | B2 | 12/2004 | Samson et al. |
| 6,896,690 | B1 | 5/2005 | Lambrecht |
| 6,929,653 | B2 | 8/2005 | Strecter |
| 6,989,027 | B2 | 1/2006 | Allen et al. |
| 7,011,681 | B2 | 3/2006 | Vesely |
| 7,267,686 | B2 | 9/2007 | Dimatteo |
| 7,329,279 | B2 | 2/2008 | Haug |
| 7,585,321 | B2 | 9/2009 | Cribier |
| 8,579,966 | B2 | 11/2013 | Seguin et al. |
| 8,663,318 | B2 | 3/2014 | Ho |
| 8,663,319 | B2 | 3/2014 | Ho |
| 2002/0013616 | A1 | 1/2002 | Carter et al. |
| 2002/0151970 | A1 | 10/2002 | Garrison et al. |
| 2003/0105517 | A1 | 6/2003 | White |
| 2004/0059412 | A1 | 3/2004 | Lytle, IV et al. |
| 2004/0215333 | A1 | 10/2004 | Duran et al. |
| 2004/0225354 | A1 | 11/2004 | Allen et al. |
| 2004/0236418 | A1 | 11/2004 | Stevens |
| 2005/0075718 | A1 | 4/2005 | Nguyen et al. |
| 2005/0137688 | A1 | 6/2005 | Salahieh |
| 2005/0154344 | A1 | 7/2005 | Chang |
| 2005/0171472 | A1 | 8/2005 | Lutter |
| 2005/0228402 | A1 | 10/2005 | Hofmann |
| 2006/0020332 | A1 | 1/2006 | Lashinski et al. |
| 2006/0025855 | A1 | 2/2006 | Lashinski et al. |
| 2006/0036317 | A1 | 2/2006 | Vidlund et al. |
| 2006/0052867 | A1 | 3/2006 | Revuelta et al. |
| 2006/0074483 | A1 | 4/2006 | Schrayer |
| 2006/0074484 | A1 | 4/2006 | Huber et al. |
| 2006/0142848 | A1 | 6/2006 | Gabbay |
| 2006/0247570 | A1 | 11/2006 | Pokorney et al. |
| 2006/0259137 | A1 | 11/2006 | Artof et al. |
| 2007/0073387 | A1 | 3/2007 | Forster et al. |
| 2007/0219630 | A1 | 9/2007 | Chu |
| 2008/0125853 | A1 | 5/2008 | Bailey et al. |
| 2008/0147160 | A1 | 6/2008 | Ghione |
| 2008/0147180 | A1 | 6/2008 | Ghione |
| 2008/0147181 | A1 | 6/2008 | Ghione |
| 2008/0200898 | A1 * | 8/2008 | Lashinski ................ 604/509 |
| 2008/0269877 | A1 | 10/2008 | Jenson et al. |
| 2009/0030503 | A1 | 1/2009 | Ho |
| 2009/0030510 | A1 | 1/2009 | Ho |
| 2009/0069886 | A1 | 3/2009 | Suri et al. |
| 2014/0142692 | A1 | 5/2014 | Ho |

FOREIGN PATENT DOCUMENTS

| | | |
|---|---|---|
| WO | WO 2007/100410 A2 | 9/2007 |
| WO | WO 2008/051554 A2 | 5/2008 |
| WO | WO 2009/052838 A1 | 4/2009 |

OTHER PUBLICATIONS

Andersen, et al. Transluminal implantation of artificial heart valves: description of a new expandable aortic valve and initial results with implantation by catheter technique in closed chest pigs. Eur Heart J 1992;13:704-708.

Bahl, et al. Balloon aortic valvuloplasty in young adults by antegrade, transseptal approach using the Inoue balloon. Cathet Cardiovasc Diagn 1998;44(3):297-301.

Bonhoeffer, et al. Percutaneous replacement of pulmonary valve in a right-ventricle to pulmonary-artery prosthetic conduit with valve dysfunction. Lancet 2000;356:1403-1405.

Boudjemline, et al. Steps toward percutaneous aortic valve replacement. Circulation 2002;105(6):775.

Carabello. Aortic Stenosis. N Engl J Med 2002;346(9):677-682.

Cribier, et al. Percutaneous transcatheter implantation of an aortic valve prosthesis for calcific aortic stenosis: first human case description. Circulation 2002;106(24):3006-3008.

Dewey, et a; Transapical Aortic Valve Implantation: an Animal Feasibility Study. Ann Thorac Surg 2006; 82(1):110-116.

Endovascular Repair of Thoracic Aortic Disease: Gore TAG Endoprothesis; Medscape.com. Mar. 15, 2010.

European search report dated Nov. 6, 2013 for EP Application No. 09800932.7.

Ferrari, et al. Transarterial aortic valve replacement with a self expanding stent in pigs. Heart 2004;90(11):1326-1331.

Gore Medical, GORE® Tri-Lobe Balloon Catheter Product Information [Technical Information]; retreived from the Internet: <http://goremedical.com/resources/dam/assets/AN0634-EN2.pdf>, 2009 W. L. Gore & Associates, Inc., 2 pages total.

Grube, et al. Percutaneous aortic valve replacement for severe aortic stenosis in high-risk patients using the second- and current third-generation self-expanding CoreValve prosthesis. J Am Coll Cardiol 2007;50:69-76.

Hanzel, et al. Retrograde Percutaneous Aortic Valve Implantation for Critical Aortic Stenosis. Catheter Cardiovasc. Interv. 2005, 64(3)' 322-326.

Ho. Percutaneous aortic valve replacement: a novel design of the delivery and deployment system. Minim Invasive Ther Allied Technol. 2008;17(3):190-194.

International search report and written opinion dated Sep. 23, 2009 for PCT/US2009/051389.

Lichtenstein, et al. Transapical transcatheter aortic valve implantation in humans: initial clinical experience. Circulation 2006;114(6):591-596.

Office action dated Feb. 4, 2011 for U.S. Appl. No. 11/781,924.
Office action dated Mar. 26, 2010 for U.S. Appl. No. 11/781,924.
Office action dated Mar. 28, 2011 for U.S. Appl. No. 12/180,223.
Office action dated Sep. 30, 2010 for U.S. Appl. No. 11/781,924.
Office action dated Oct. 9, 2013 for U.S. Appl. No. 12/180,223.
Office action dated Oct. 29, 2010 for U.S. Appl. No. 12/180,223.

Salizzoni, et al. Transapical off-pump removal of the native aortic valve: A proof-of concept animal study. J Thorac Cardiovasc Surg, Aug. 2009;138:468-473.

Vandenberghe, et al. In Vitro Testing of a Temperary Catherter-Based Aortic 'Parachute' Valve. ASAIO Journal 2008, v. 54, 574-577.

Velling, et al Colonic Stent Placement Facilitated by Percutaneous Cecostomy and Antegrade Enema. American Journal of Roentgenology 2000; 175:119-120.

Webb, et al. Percutaneous aortic valve implantation retrograde from the femoral artery. Circulation 2006;113:842-850.

Zoghbi, et al. Recommendations for evaluation of the severity of native valvular regurgitation with two-dimensional and Doppler echocardiography. J Am Soc Echocardiogr 2003;16:777-802.

(56) References Cited

OTHER PUBLICATIONS

Notice of allowance dated Nov. 27, 2013 for U.S. Appl. No. 11/781,924.
Notice of allowance dated Dec. 19, 2013 for U.S. Appl. No. 12/180,223.
Office action dated Jun. 24, 2015 for U.S. Appl. No. 14/154,890.
Office action dated Oct. 8, 2015 for U.S. Appl. No. 14/154,890.
Office action dated Dec. 21, 2015 for U.S. Appl. No. 14/154,890.

* cited by examiner

METHOD AND APPARATUS FOR PERCUTANEOUS AORTIC VALVE REPLACEMENT

CROSS-REFERENCE TO RELATED APPLICATIONS

This application is a continuation application of U.S. patent application Ser. No. 11/781,924, filed Jul. 23, 2007 and entitled "Method and Apparatus for Percutaneous Aortic Valve Replacement," which is incorporated herein by reference in its entirety and to which application priority is claimed under 35 U.S.C. §120.

This application is related to the following co-pending and co-assigned patent applications: U.S. patent application Ser. No. 12/180,223, filed Jul. 25, 2008 and entitled "Methods and Apparatus for Percutaneous Aortic Valve Replacement", and U.S. patent application Ser. No. 13/227,276, filed Sep. 7, 2011 and entitled "Method and System for Balloon Counterpulsation During Aortic Valve Replacement," the contents of which are incorporated herein by reference.

FIELD OF INVENTION

The technical field of this disclosure is medical procedures and devices. More specifically, this disclosure describes a system for the percutaneous delivery and deployment of aortic replacement valves facilitated by a temporary aortic valve.

BACKGROUND OF THE INVENTION

The current standard of care for patients with significant aortic valve disease is still surgical aortic valve replacement. As the treatment of many cardiovascular diseases has become minimally invasive and catheter-based, endovascular techniques and equipment has led to the development of percutaneous aortic valve (PAV) replacement as a potential clinical reality. PAV replacement is currently an investigational procedure.

The notion of PAV replacement was first introduced in 1992 by Andersen et al in a swine model [Andersen H R et al., Eur Heart J 1992; 13:704-7081]. The first human implantation of a percutaneous valved-stent was performed in the pulmonic position as reported by Bonhoeffer et al., in 2000 [Bonhoeffer P, et al., Lancet 2000; 356:1403-1405]. The first human implantation of a PAV was described in 2002 using a valved-stent design by Cribier et al via the antegrade/inter-atrial septal puncture approach [Cribier A, et al., Circulation 2002; 106 (24):3006-3008]. Other techniques such as retrograde and transapical approaches of delivery and deployment of the PAV were later introduced [Webb J G, et al., Circulation 2006; 113:842-850; Lichtenstein S V, et al., Circulation 2006; 114 (6):591-596].

In the PAV replacement procedure, most of the cardiac complications occur at the required precise placement of the PAV during implantation. Due to the aortic valve's close proximity to the coronary ostia on one side, and the mitral valve on the other, misalignment of the PAV can cause serious compromise of coronary or mitral valve function [Boudjemline Y, et al., Circulation 2002; 105 (6):775; Ferrari M, et al., Heart 2004; 90 (11):1326-1331]. The significant hemodynamic forces encountered at the left ventricular outflow tract to the ascending aorta, together with the anatomic structures comprising the native valve, add to the difficulty of precise placement of the PAV and the risk of device embolization.

Objects of the present invention include providing a PAV delivery and deployment system that demonstrates structural integrity and that includes specific features to optimize precise PAV placement and deployment while maintaining patient stability. Precise PAV placement and deployment can be facilitated by removing anatomic structures that can hinder or interfere with precise PAV placement, and by minimizing the hemodynamic forces encountered by the surgeon during the PAV replacement procedure. Maintaining patient stability during the replacement procedure can be facilitated by providing a substitute valve that promotes coronary perfusion while moderating stresses (aortic insufficiency and aortic stenosis) experienced by cardiac muscle prior to the PAV becoming operational.

SUMMARY OF THE INVENTION

These and other problems are solved by the subject invention, a novel method for percutaneous aortic valve replacement that employs a novel temporary aortic valve.

Salient features of the PAV delivery and deployment system of the present invention are the capability to (1) achieve an adequately stable physiologic and anatomic environment for device positioning and deployment, and (2) maintain sustainable hemodynamic conditions allowing for the completion of the procedure without undue patient instability. To achieve a stable environment for both the PAV implantation and patient safety, a temporary "aortic valve" is introduced into the ascending aorta. To simplify the local anatomy allowing for a relative unobstructed PAV placement, pre-dilation and ablation of the native aortic valve precedes PAV delivery and deployment.

The novel apparatus of the subject invention comprises a temporary aortic valve (TAV) having a plurality of inflatable balloon means. The balloon means are contiguously arranged around a central catheter. The TAV and its central catheter, with balloons deflated, is advanced over a guide wire to a position within the ascending aorta just above the Sinus of Valsalva and coronary ostia.

Once inflated, the TAV functions as a valve allowing limited blood flow in a forward direction, up through the coronary arteries and ascending aorta during systole. During diastole, the TAV functions to limit backflow into the left ventricle while still allowing continued perfusion in the coronary arteries.

The TAV promotes patient stability during the PAV replacement procedure in at least two ways. First, use of the TAV promotes continuous coronary perfusion during native valve ablation and replacement. Second, use of the TAV in place of the ablated native stenotic aortic valve minimizes the stress encountered by the cardiac muscle due to partial alleviation of the transvalvular pressure gradient.

In addition, the contiguous design of the TAV with central catheter provides a reliable vehicle demonstrating structural integrity for the delivery and deployment of the PAV device and related procedural tools.

The novel method of the subject invention involves pre-dilation of the native aortic valve followed by ablation (removal) of the native valve by pressing and compressing the native valve leaflets against the walls of the aortic annulus, all with the TAV in place.

More particularly, the method comprises the steps of crossing the native aortic valve with a guide wire in conventional retrograde fashion; advancing the TAV with central catheter over the guide wire within the ascending aorta; positioning and the TAV within the ascending aorta just above the Sinus of Valsalva where it is inflated; advancing a pre-dilation balloon through the TAV central catheter and over the guide wire to a position across the native aortic valve; inflating the pre-dilation balloon to dilate the diseased native valve and then withdrawing the pre-dilation balloon; advancing an ablation stent with stent catheter into position across the native valve; deploying the ablation stent to ablate the native valve pedals against the walls of the aortic annulus and then withdrawing the stent catheter; advancing a percutaneous bio-prosthetic aortic valve (PAV) with deployment catheter into position within the aortic annulus, deploying the PAV and then withdrawing the PAV deployment catheter and any remaining deployment tools; and finally deflating and withdrawing the TAV and guide wire.

Further objects and advantages of this invention will become apparent from consideration of the drawings and ensuing description.

DETAILED DESCRIPTION OF THE PRESENTLY PREFERRED EMBODIMENTS

Temporary Aortic Valve

Figures 1, 2:
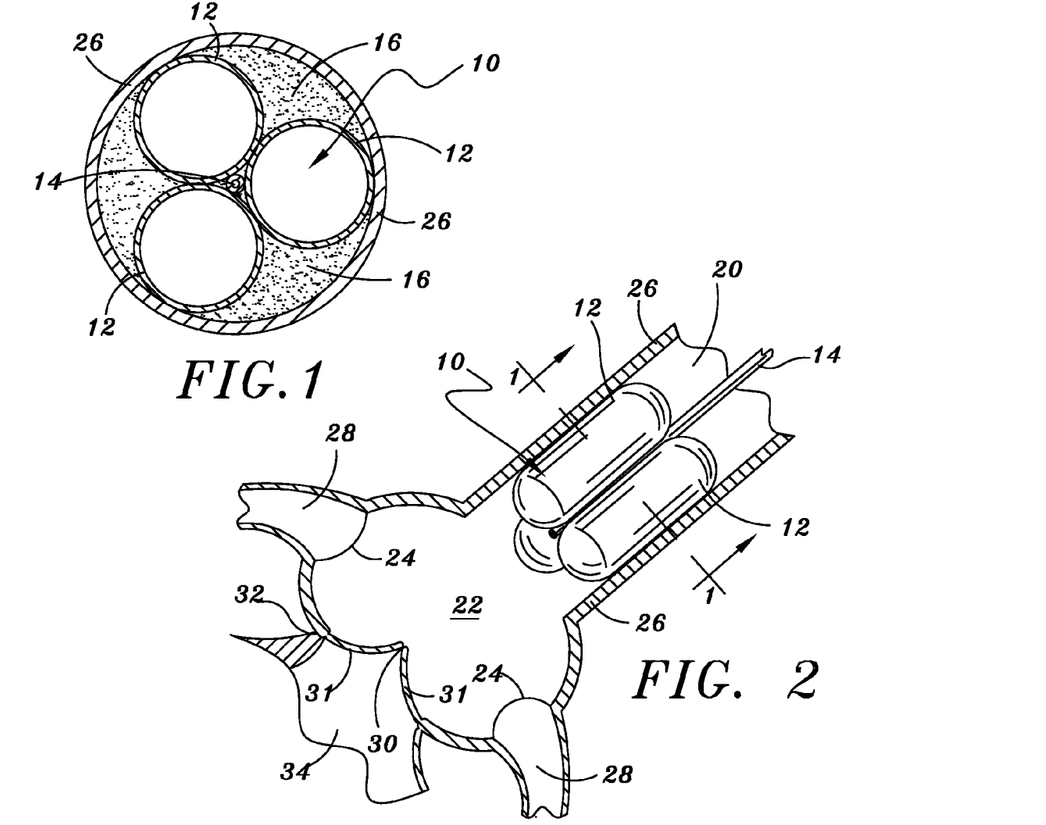
FIG. 1 illustrates in cross-sectional view, taken along line 1-1 of FIG. 2, the temporary aortic valve (TAV) of the present invention. The TAV is shown fully deployed, inflated against the inside wall of the ascending aorta, leaving gaps (shaded area) for continuous blood flow.
FIG. 2 shows in longitudinal (axial) view the TAV system of the present invention deployed within the ascending aorta, positioned just above (downstream from) the Sinus of Valsalva and coronary ostia.

Illustrated in FIG. 1 in cross section and FIG. 2 in side view is the temporary aortic valve (TAV) 10 of the present invention. According to the preferred embodiment shown, TAV 10 is comprised of three elongated supporting-balloons 12 of equal shape and size, contiguously arranged in parallel around a central guiding-catheter mechanism 14.

TAV 10 is placed within the ascending aorta 20 by means of catheter 14, and then inflated. FIG. 2 depicts TAV 10 deployed to a position within ascending aortic 20 just above (downstream from) the Sinus of Valsalva 22 and the coronary ostia 24. Once in position, supporting balloons 12 are inflated such that TAV 10 is lodged firmly against the inside walls 26 of ascending aorta 20.

Central catheter 14 sitting within the multi-balloon TAV 10 can be fashioned to the necessary French-size to accommodate the PAV device and related tools. The contiguous design of TAV 10 and central catheter 14 provide added mechanical stability and support for the delivery and deployment the PAV device as well as the tools (described below) used to prepare the aortic annulus for PAV implantation.

The gaps 16 shown shaded in FIG. 1, between the supporting balloons 12 and aortic wall 26, allow limited blood flow, creating temporary effective aortic insufficiency (AI) and aortic stenosis (AS). As explained below, the temporary AI (during diastole) and AS (during systole) thus created are deliberately designed to serve important functions during the percutaneous aortic valve (PAV) implant procedure.

Figure 3:
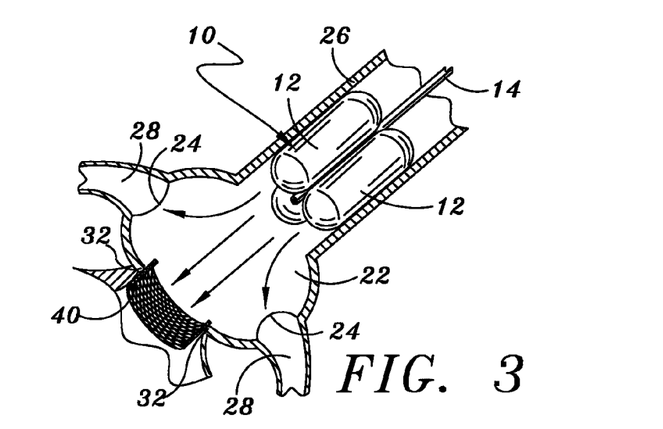
FIG. 3 illustrates the fluid dynamics of the TAV system of the present invention positioned within the ascending aorta as shown in FIG. 2, during diastole, with the native aortic valve ablated and ablation stent in place.

FIG. 3 shows the fluid dynamics of the method of the present invention, with TAV 10 deployed in position, during diastole. The arrows depict limited retrograde blood flow from TAV 10 back into the left ventricle 34 (shown in FIG. 2) while permitting coronary perfusion through ostia 24. Accordingly, TAV 10 limits the amount of AI into left ventricle 34 while allowing for continued diastolic filling of the coronary arteries 28.

Figures 4, 5:
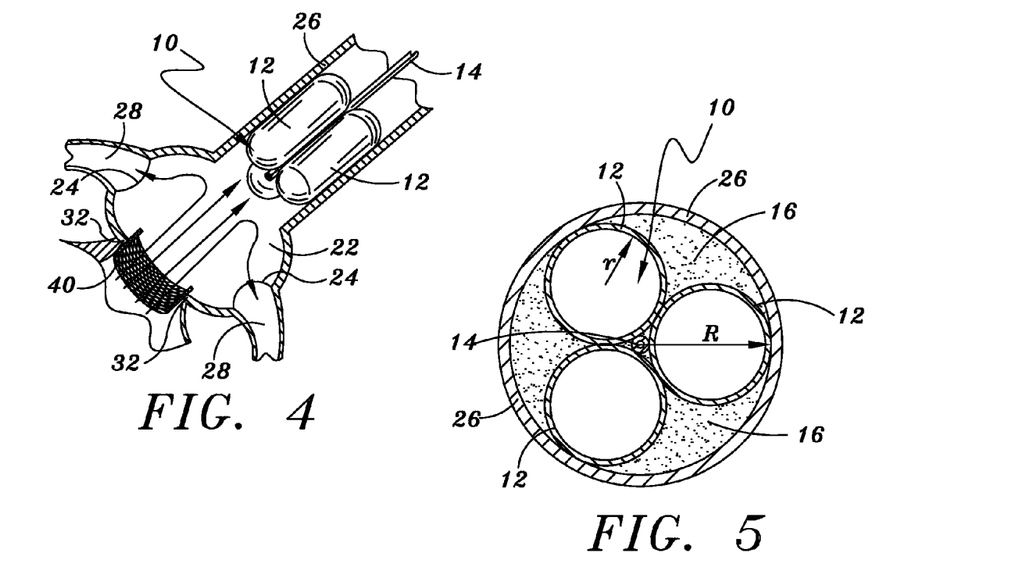
FIG. 4 illustrates the fluid dynamics of the deployed TAV system of the present invention positioned as in FIG. 2, during systole, with the native aortic valve ablated and ablation stent in place.
FIG. 5 shows the fully deployed TAV in cross section, taken along line 1-1 of FIG. 2, illustrating the radius of the TAV balloon components (assuming all balloons are of equal radius) relative to the radius of the ascending aorta, and gaps (shaded area) that permit continuous blood flow.

The native aortic valve 30 comprised of valve leaflets 31 is shown in FIG. 2. Substituted therefore in FIGS. 3 and 4 is an ablation stent 40, lodged within the aortic annulus 32, following ablation of native aortic valve 30 and leaflets 31. Ablation of the tissues of native valve 30 into the aortic annulus is an important step in the PAV implantation procedure further discussed below.

Once the native valve 30 tissues have been ablated as shown in FIGS. 3 and 4, acute wide-open AI occurs at the level of aortic annulus 32. Meanwhile, TAV 10 serves as a control valve for the amount of AI rushing back to left ventricle 34. Massive acute AI during systole is prevented, thereby maintaining patient stability, as further demonstrated by the Mathematical Considerations set forth below.

FIG. 4 illustrates the fluid dynamics of the method of the present invention with TAV 10 deployed during systole. The arrows depict partially obstructed blood flow through TAV 10 and unobstructed flow into coronary arteries 28. TAV 10 allows for temporary pressure build-up in the region of Sinus of Valsalva 22, enhancing partial systolic coronary perfusion. After native valve 30 (shown in FIG. 2) is ablated, the pressure gradient along the flow path is relocated from native valve 30 to TAV 10.

As demonstrated by the Mathematical Considerations set forth below, the AS at TAV 10 will be less than the critical value at the native aortic valve stenosis. Because TAV 10 is located above the level of coronary ostia 24, TAV 10 serves two major purposes. First, TAV 10 can enhance partially the systolic filling of coronary arteries 28. More importantly, after native aortic valve 30 (shown in FIG. 2) is ablated, eliminating the native aortic stenosis, the lower degree of AS offered by TAV 10 will immediately relieve the effective transvalvular pressure gradient as illustrated in FIG. 4. Lastly, because wide-open blood flow is prevented within the ascending aorta between left ventricle 34 (shown in FIG.

2) and TAV 10, the relative quiescent hemodynamic conditions, along with the open channel created by ablation stent 40 at the aortic annulus 32 (as depicted in FIGS. 3 and 4), allow for fine positioning, placement and deployment of the PAV within this region.

Mathematical Considerations of AI/AS At the Temporary Aortic Valve

Referring to cross-sectional illustration FIGS. 1 and 5, the shaded areas represent gaps 16 between the inflated TAV balloons 12 and aortic wall 26. Gaps 16 also reflect the effective AI and AS, created during diastole and systole respectively, following inflation of TAV 10 against aortic wall 26.

Referring to FIG. 5, the calculation of the effective AI and AS at TAV 10 is as follows:

R=radius of ascending aorta 20 r=radius of a supporting balloons 12; all three balloons 12 according to the embodiment illustrated being of equal size and shape R~2.15 r (by simple geometry), assuming adequate apposition of balloons 12 to aortic wall 26

Shaded area (gaps 16) for blood flow~35% of the cross-sectional area of ascending aorta 20

Well documented physiologic significant AI begins at >60% of the cross-sectional area of aortic annulus 32, as measurable by Doppler echocardiography in the parasternal short-axis view [Zobhbi W A, et al., *J Am Soc. Echocardiogr* 2003; 16:789]. Assuming application of TAV 10 positioned and deployed within ascending aorta 20 as shown, the calculated effective AI of 35% is categorized as moderate range in severity and should be well-tolerated by the patient even if it occurs acutely, e.g., after complete ablation of native aortic valve 30.

Clinical significant AS is considered when the aortic valve area (AVA) is reduced to below 25% of its original cross-sectional area [Carabello B, *N Engl J Med* 2002; 346 (9):677-682]. For example, a normal adult aortic orifice area is approximately 3 $cm^2$, and a calculated AVA of less than 0.75 $cm^2$ is considered significant. The calculated effective AS of TAV 10 of 35% falls within the moderate range, and should be an improvement from the patient's original condition of critical native aortic stenosis and should be well-tolerated.

The amount of effective AI and AS created by TAV 10 during diastole and systole, respectively, may be altered by varying the numbers, size and/or shapes of supporting balloons means 12.

According to one preferred embodiment of the subject invention, TAV 10 is comprised of plurality of inflatable means 12 having a shape and size such that, when inflated and lodged against aortic wall 26, gaps 16 are created reflecting approximately 35% of the cross-sectional area of ascending aorta 20.

According to a further preferred embodiment of the subject invention, TAV 10 is comprised of plurality of inflatable means 12 having a shape and size such that, when inflated and lodged against aortic wall 26, gaps 16 are created reflecting between 0% and 60% of the cross-sectional area of ascending aorta 20.

According to a further preferred embodiment of the subject invention, TAV 10 is comprised of plurality of inflatable means 12 having a shape and size such that, when inflated and lodged against aortic wall 26, gaps 16 are created reflecting between 25% and 100% of the effective aortic valve area (AVA)

According to a further preferred embodiment of the subject invention, TAV 10 is comprised of plurality of inflatable means 12 having a shape and size such that, when inflated and lodged against aortic wall 26, gaps 16 are created reflecting between 25% and 60% of the effective aortic valve area (AVA).

According to a further preferred embodiment of the subject invention, TAV 10 is comprised of plurality of inflatable means 12 having a shape and size such that, when inflated and lodged against aortic wall 26, gaps 16 are created the total cross-sectional area which is at least 0.75 $cm^2$ in the case of an adult patient.

Method of Replacement of the Native Aortic Valve

Figure 6:
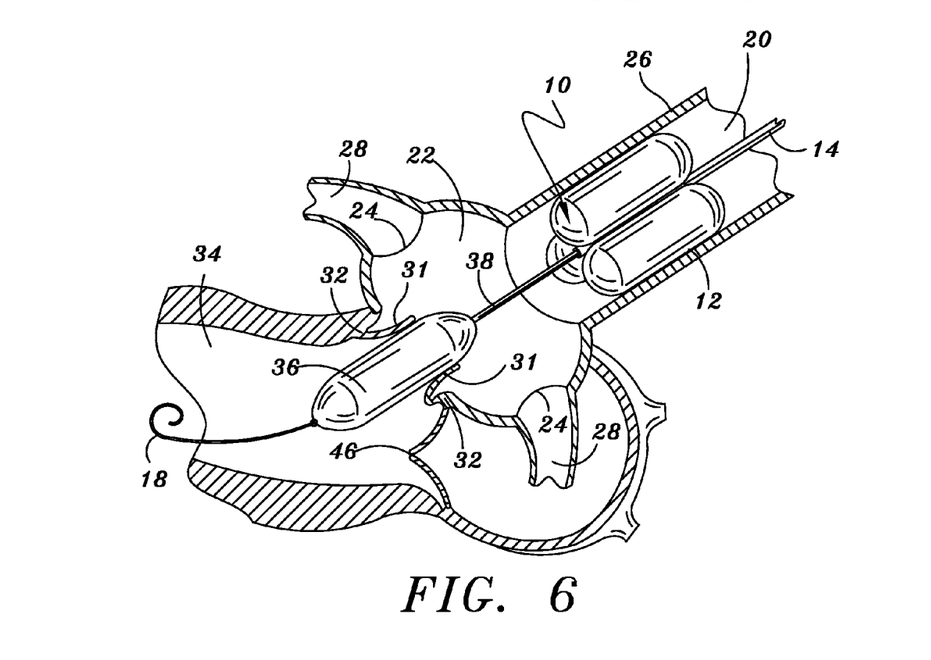
FIG. 6 shows the step of the percutaneous aortic valve (PAV) replacement procedure involving predilation of the native aortic valve using a conventional valvuloplasty balloon in preparation for valve ablation.
Figure 7:
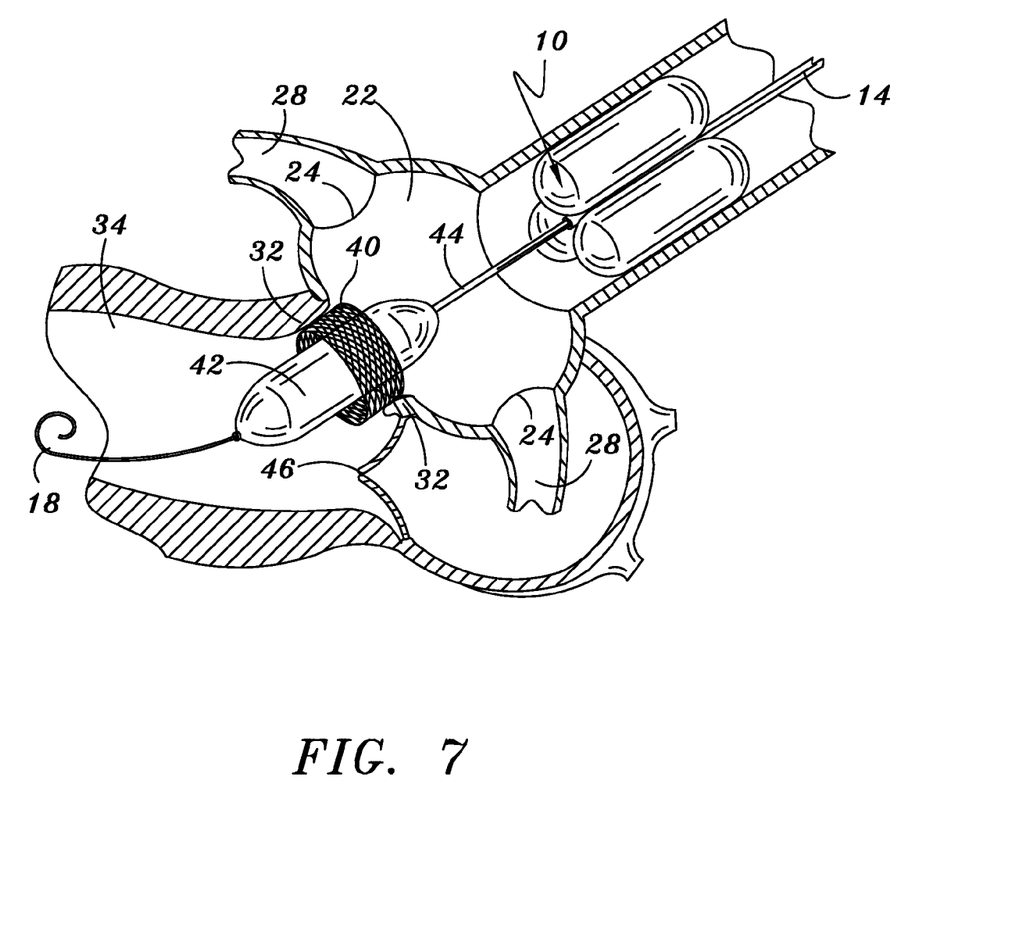
FIG. 7 illustrates the subsequent step of the PAV replacement procedure wherein the native aortic valve is entrapped and ablated against the aortic annulus using a balloon mounted ablation stent.
Figure 8:
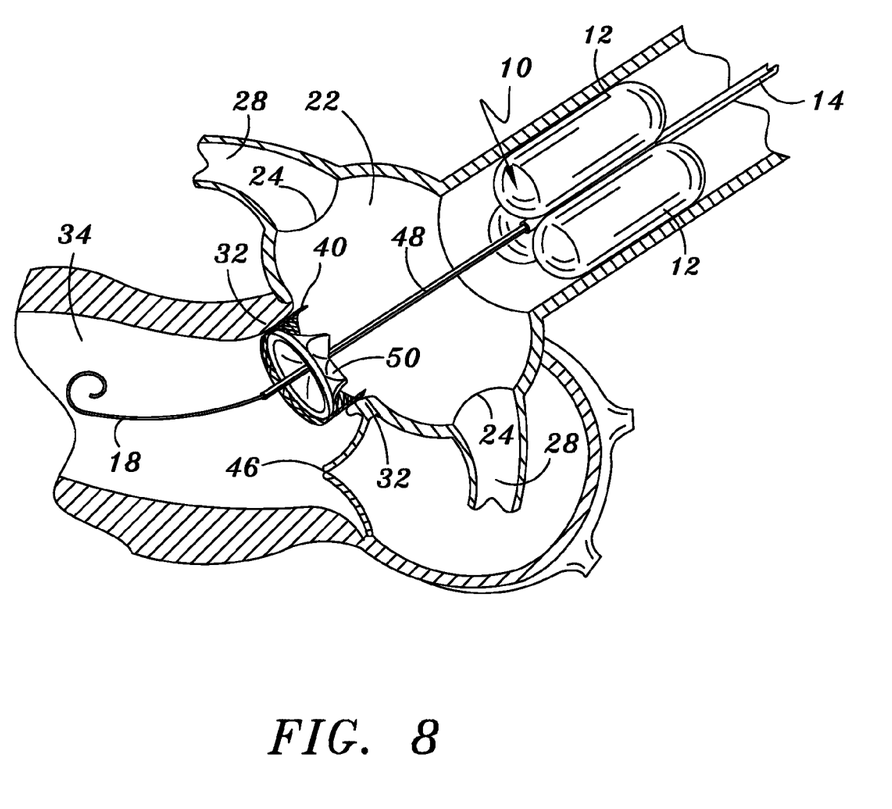
FIG. 8 illustrates the step of the PAV replacement procedure during which the PAV is delivered, positioned, and deployed at the site of the native aortic valve inside the ablation stent. The TAV remains inflated during PAV positioning and deployment thereby moderating the hydrodynamic forces, encouraging coronary perfusion, and reducing the pressure gradient experienced by the heart muscle.

The method of the subject invention is illustrated in FIGS. 6 through 8.

The materials and methods for the percutaneous introduction of catheters, stents, lumen and related surgical tools into the ascending aorta from the femoral artery are well known to those who practice in the field. The method of the subject invention assumes and incorporates by this reference all such familiar and conventionally employed materials and methods.

Referring to FIG. 6, the procedure for implantation of a percutaneously delivered prosthetic aortic valve (PAV) begins with crossing native aortic valve 30 with a guide wire 18 in a retrograde fashion. TAV 10, in deflated mode, is advanced to position within ascending aorta 20 over guide wire 18 by means of central catheter 14. Supporting balloons 12 of TAV 10 are inflated to adequate apposition to aortic wall 26.

Once inflated, TAV 10 is operational, functioning as a temporary valve to facilitate the remainder of the PAV implantation procedure. As explained above, TAV 10 provides an environment of tolerable AI and AS following ablation of the native aortic valve and during positioning and placement of the bio-prosthetic replacement valve.

The remaining tools for the valve replacement procedure are transported over guide wire 18 within central catheter 14, and within further particularized catheters or stents that are specific to the tool in question. The stable conduit provided by TAV 10 with balloons 12 fully inflated and lodged against aortic walls 26 facilitates the reliable transportation of these remaining PAV implantation tools.

FIG. 6 also illustrates the step of pre-dilation of stenotic native aortic valve 30 in order to prepare valve 30 for ablation. A conventional valvuloplasty balloon 36 of the type commercially available [Bahl V K, et al., *Cathet Cardiovasc Diagn* 1998; 44 (3):297301], is built on a delivery catheter 38 and advanced over guide wire 18 through central catheter 14. Once in position across native aortic valve 30, balloon 36 is inflated, dilating native valve 30. Following valve 30 dilation, balloon 36 with catheter 38 is withdrawn.

Ablation of native aortic valve 30, the next step in the percutaneous valve replacement procedure, employs an aortic annulus stent 40. Ablation of native valve 30 with annulus stent 40 prior to PAV implantation greatly facilitates the precise and reliable positioning and placement of the PAV by providing an unobstructed path and platform for PAV implantation as compared with the conventional procedure, wherein the PAV is positioned and deployed in the presence of native aortic valve 30 with the valve leaflets 31 intact (as shown in FIG. 2).

As illustrated in FIG. 7, ablation stent 40 with a stent deployment balloon 42 is advanced to the site of native aortic valve 30 by means of a stent catheter 44 over guide wire 18 and through central catheter 14. Once in place, ablation stent 40 is deployed through inflation of deployment balloon 42, displacing and entrapping native valve 30 with leaflets 31 against aortic annulus 32. Ablation stent 40 with deployment balloon 42 functions in a manner analogous to coronary stents used in the treatment of atherosclerotic plaques. Ablation stent 40 remains permanently in position within aortic annulus 32 while deployment balloon 42 and stent catheter 44 is withdrawn.

The final step in the method of the subject invention, placement of a percutaneous aortic valve (PAV) 50, is illustrated in FIG. 8. Aortic annulus 32 has been optimized for PAV 50 placement by addressing two significant obstacles: diseased valve 30, removed through deployment of ablation stent 40 (FIG. 7), and the hemodynamic pressure gradient, relocated and minimized (as shown in FIGS. 3 and 4) through deployment of TAV 10.

PAV 50 with a deployment catheter 48 is advanced over guide wire 18 through central catheter 14 until in position within aortic annulus 32 and ablation stent 40. PAV 50 can now be ideally positioned clear of the mitral valve 46 and coronary ostia 24, and deployed by means of catheter 48 precisely, with minimal undue axial movements and relative ease.

Once PAV 50 been deployed into position within ablation stent 40 which itself is lodged within aortic annulus 32, deployment catheter 48 and any remaining deployment tools can be withdrawn over guide wire 18 through central catheter 14. TAV 10 can then be deflated and withdrawn. Alternatively, TAV 10 can be left in position, temporarily, while the performance of PAV 50 is monitored during post-op and healing. Withdrawal of central catheter 14 and guide wire 18 completes the procedure.

Summary and Scope

The invention disclosed and described above presents an empirical design for a PAV replacement system offering a novel, viable and improved technology for the delivery and deployment of the currently available percutaneous aortic valves or valved stents.

The greatest pitfalls of the PAV replacement procedure are the close proximity of vital structures such as the mitral valve apparatus and the coronary ostia, and the difficulty to correctly position the PAV device in an environment of high velocity flow, turbulence, and anatomic obstacle of the diseased native valve.

The multi-balloon configured temporary aortic valve apparatus of the present invention relocates the highest pressure gradient downstream to the ascending aorta following ablation of the native valve. The multi-balloon TAV allows for a more quiescent hemodynamic environment at the aortic annulus level for PAV positioning, while providing adequate coronary perfusion during the cardiac cycle. Ablating the native aortic valve with an ablation stent removes the obstructive nature of the diseased valve structure, further facilitating the delicate placement of the PAV.

The central guiding catheter mechanism, with the multi-balloon TAV mounted at the tip, can be fashioned to the necessary French-size to accommodate the PAV device and related tools. The contiguous design of the TAV and the central guiding catheter provide added mechanical stability and support for the delivery and deployment of the predilatation balloon, the valve ablation stent, and the PAV device with deployment tools. Left ventricular trauma leading to cardiac tamponade from rigid guide wires have been reported as a significant source of periprocedural complication [Grube E et al., *J Am Coll Cardiol* 2007; 50:69-768]. The substantial mechanical support provided by the TAV-guiding catheter system decreases the need for a more aggressive and stiff guide wire for equipment transport.

The valve ablation stent is designed and constructed to have adequate radial strength to entrap and hold the native diseased aortic valve tightly against the annulus. These stents may have drug-elution capability. Currently available PAV devices may need to be reconfigured to fit securely into the valve ablation stent within the aortic annulus.

The disclosed PAV delivery and deployment system of the present invention, as with some current models, can also be used to replace the aortic valve in severe aortic insufficiency without stenosis. In isolated aortic insufficiency, predilatation prior to placement of the ablation stent may or may not be necessary. Case selection in this group of patients, however, may occasionally be somewhat challenging depending on the degree of pre-existing left ventricular dysfunction.

Design limitations of the presented system may exclude its use in patients with ascending aortic aneurysm or severe aortic root dilatation, severe isolated aortic insufficiency with end-staged cardiomyopathy, and perhaps the excessively bulky calcified aortic valve. In the case of severe aortic insufficiency without stenosis and end-stage cardiomyopathy, the patient may not tolerate the required transient effective moderate-range aortic stenosis created by the TAV in the ascending aorta. In the case of the excessively calcified aortic valve, adequate entrapment and ablation of the native valve may be difficult; adequate lumen for PAV implantation may be compromised in this scenario.

While the present invention has been described in terms of specific structures, specific configurations of structures, and specific method steps, representing the currently understood preferred embodiments, the invention should not be conceived as limited to these specific structures, configurations or steps.

By way of example and not limitation, two or more than three balloons 12 may be substituted for the three balloons 12 comprising TAV 10 shown in FIGS. 1 through 8, and the size and shape of balloons 12 can be varied, absolutely or relative to one another. It should be clear to those schooled in the relevant art who consider this disclosure that the degree of AI and AS can be varied by varying the number, size and shape of balloons 12. Clinical circumstances may dictate different degrees of AI and AS for different patients, and patient aortic diameters differ. Optimal AI and AS for a given patient is achievable through the selection of number, size and shape of balloons 12.

Similarly, although the use of inflatable balloons in percutaneous circulatory procedures is well known and understood, alternative materials that can be alternatively expanded and compressed and that provide equivalent or superior functionality and utility to partially occlude the ascending aorta may be substituted for balloons 12 without departing from the spirit and scope of the subject invention.

Concerning the disclosed method, any of the various surgical tools and methodologies that have been disclosed or practiced in the fields of circulatory and cardiac medicine and, in particular, those tools and methodologies that are familiar to those who practice in the field of percutaneous cardiac procedures, may be substituted for the specific pre-dilation, ablation and PAV deployment tools, and the specific methodologies, described and depicted in the preferred embodiments disclosed herein, and all such substitutions and alternative tools and procedures being within the subject invention as contemplated. By way of example and not by way of limitation, the method of the subject invention involving ablation of the native valve in advance of PAV positioning and implantation may be used with some of the other disclosed steps omitted, or with steps not specifically disclosed herein substituted for certain disclosed steps. Similarly, the method of the subject invention may be used in conjunction with apparatus other than the TAV and PAV implantation tools specifically described above.

Accordingly, while the embodiments of the invention disclosed herein are presently considered to be preferred, various changes and modifications can be made without departing from the spirit and scope of the invention. The scope of the invention should be determined by the appended claims and their legal equivalents, rather than with reference to any particular example, embodiment or illustration.

The invention claimed is:

1. A method for percutaneous aortic valve replacement comprising:
   providing a temporary aortic valve comprising a central catheter mechanism and a plurality of expandable elements distributed around the catheter mechanism, the temporary aortic valve having a collapsed mode and a fully expanded mode;
   advancing the temporary aortic valve over a guide wire in the deflated mode to a position within the ascending aorta above a Sinus of Valsalva and coronary ostia of the patient;
   deploying the temporary aortic valve within the ascending aorta by fully expanding the plurality of expandable elements to lodge the temporary aortic valve against an inner wall of the ascending aorta, thereby placing the temporary aortic valve in the fully expanded mode, wherein in the fully expanded mode at least a surface of the fully expanded plurality of expandable elements is in contact with an inner wall of the ascending aorta while only partially occluding the ascending aorta and wherein gaps formed between the temporary aortic valve in the fully expanded mode in the ascending aorta and the inner wall of the ascending aorta provide for continuous blood perfusion therethrough; wherein the cross-sectional area of the gaps falls within a range of between 25% and 60% of a cross sectional area of the ascending aorta;
   pre-dilating a native aortic valve and ablating the native aortic valve of a patient while the temporary aortic valve is in the fully expanded mode within the ascending aorta; and positioning and implanting a permanent replacement percutaneous aortic valve within a native aortic annulus of the pre-dilated and ablated native aortic valve while the temporary aortic valve is in the fully expanded mode within the ascending aorta.

2. The method of claim 1, wherein the native aortic valve is ablated through deployment of an ablation stent that remains within the aortic annulus and that receives and retains the percutaneous aortic valve.

3. The method of claim 1, wherein the step of deploying a temporary aortic valve within the ascending aorta above the Sinus of Valsalva and coronary ostia causes controlled aortic stenosis.

4. The method of claim 1, wherein the step of deploying a temporary aortic valve within the ascending aorta above the Sinus of Valsalva and coronary ostia causes controlled aortic insufficiency.

5. A method for percutaneous aortic valve replacement comprising the steps of:
   a. Percutaneously introducing a guide wire into the an ascending aorta of a patient and crossing the a native aortic valve of the patient with the guide wire;
   b. Providing a temporary aortic valve comprising a central catheter mechanism and a plurality of expandable elements distributed around the catheter mechanism, the temporary aortic valve having a collapsed mode and a fully expanded mode;
   c. Advancing the temporary aortic valve over the guide wire into a position within the ascending aorta above a Sinus of Valsalva and coronary ostia of the patient;
   d. Deploying the temporary aortic valve within the ascending aorta by fully expanding the plurality of expandable elements to lodge the temporary aortic valve against an inner wall of the ascending aorta, thereby placing the temporary aortic valve in the fully expanded mode, wherein in the fully expanded mode at least a surface of the fully expanded plurality of expandable elements is in contact with an inner wall of the ascending aorta while only partially occluding the ascending aorta, and wherein gaps formed between the temporary aortic valve in the fully expanded mode in the ascending aorta and the inner wall of the ascending aorta provide for continuous blood perfusion therethrough;
   e. Advancing a pre-dilation device into a position through a catheter lumen of the central catheter mechanism across the native aortic valve;
   f. Dilating the native aortic valve using the pre-dilation device and then withdrawing the pre-dilation device through the catheter lumen;
   g. Advancing an ablation stent through the catheter lumen into a position across the native aortic valve;
   h. Deploying the ablation stent to ablate the native aortic valve with leaflets against walls of an aortic annulus, wherein the ablation stent remains within the aortic annulus to receive and retain replacement aortic valve;
   i. Advancing the replacement aortic valve using a deployment means within the catheter lumen into a position within the aortic annulus, wherein the ablation stent receives and retains the replacement aortic valve;
   j. Deploying the replacement valve within the aortic annulus using the deployment means through the catheter lumen; and
   k. Withdrawing the deployment means through the catheter lumen; and
   l. Withdrawing the temporary aortic valve and the guide wire.

6. The method of claim 5 wherein a cross-sectional area of the gaps formed between and resulting from the configuration of the plurality of expandable elements in the temporary aortic valve when in the fully inflated mode represents about 35% of a cross-sectional area of the ascending aorta.

7. The method of claim 5 wherein a cross-sectional area of the gaps formed between and resulting from the configuration of the plurality of expandable elements in the temporary aortic valve when in the fully inflated mode falls within a range of between 25% and 60% of an effective aortic valve area.

8. The method of claim 5 wherein a cross-sectional area of the gaps formed between and resulting from the configuration of the plurality of expandable elements in the temporary aortic valve when in the fully inflated mode is at least 0.75 cm$^2$ in the case of an adult patient.

9. The method of claim 5 wherein the temporary aortic valve comprises three balloons of equal size and shape.

10. The method of claim 5 wherein the plurality of balloons are of unequal size and shape.

11. The method of claim 5 wherein one or more of the following have drug elution capacities: the central catheter mechanism, the temporary aortic valve, the pre-dilation device, the ablation stent, and the replacement valve deployment means.

12. The method of claim 5, wherein the steps of:
 e. Advancing a pre-dilation device into a position through the catheter mechanism lumen across the native aortic valve, and
 f. Dilating the native aortic valve using the pre-dilation device and then withdrawing the device through the catheter lumen, are performed prior to the steps of:
 c. Advancing the temporary aortic valve over the guide wire into a position within the ascending aorta above a Sinus of Valsalva and coronary ostia of the patient; and
 d. Deploying the temporary aortic valve within the ascending aorta by fully expanding the plurality of expandable elements to lodge the temporary aortic valve against an inner wall of the ascending aorta, thereby placing the temporary aortic valve in the fully expanded mode, wherein in the fully expanded mode at least a surface of the fully expanded plurality of expandable elements is in contact with an inner wall of the ascending aorta while only partially occluding the ascending aorta, and wherein gaps formed between the temporary aortic valve in the fully expanded mode in the ascending aorta and the inner wall of the ascending aorta provide for continuous blood perfusion therethrough.

13. A method for percutaneous aortic valve replacement, the method comprising:
 providing a temporary aortic valve comprising an expandable means, wherein fully expanding the expandable means fully expands the temporary aortic valve;
 fully expanding the temporary aortic valve in an ascending aorta such that the fully expanded temporary aortic valve is in touching contact with inside walls of the ascending aorta of a patient while only partially occluding the aorta;
 wherein the fully expanded temporary aortic valve in the ascending aorta of the patient leaves gaps for continuous blood perfusion, and
 wherein a cross-sectional area of the gaps falls within a range of between 25% and 60% of a cross sectional area of a native aortic valve; and
 wherein the temporary aortic valve remains fully expanded and in touching contact with inside walls of the ascending aorta until it is withdrawn from and no longer disposed in the ascending aorta of the patient.

14. The method of claim 13, wherein fully expanding the temporary aortic valve comprises expanding an expandable occlude of the temporary aortic valve, and wherein the expandable occlude surrounds a central catheter mechanism of the temporary aortic valve.

15. The method of claim 14, further comprising advancing a valve replacement tool through the central catheter mechanism.

16. The method of claim 13, further comprising ablating a native aortic valve against walls of an aortic annulus.

17. The method of claim 16, further comprising dilating the native aortic valve before ablating the native aortic valve.

18. The method of claim 13, further comprising deploying a replacement valve within an aortic annulus.

19. The method of claim 13, wherein the native aortic valve area is about 3 $cm^2$ and a cross-sectional area of the gaps left by the fully expanded temporary aortic valve is at least 0.75 $cm^2$.

20. The method of claim 13, further comprising positioning the temporary aortic valve within the ascending aorta just above the Sinus of Valsalva and coronary ostia prior to fully expanding the temporary aortic valve.

21. The method of claim 13, wherein the inflatable means comprises a plurality of inflatable balloons.

22. The method of claim 21, wherein the inflatable means comprises three balloons arranged to provide gaps therebetween to allow continuous blood perfusion.

23. The method of claim 22, wherein the three balloons are of equal size.

24. The method of claim 22, wherein the three balloons are of unequal size.

* * * * *